United States Patent
Lyell

[11] Patent Number: 6,080,167
[45] Date of Patent: Jun. 27, 2000

[54] ANASTOMOTIC INSTRUMENT

[76] Inventor: Mark S. Lyell, 3501 Montgomery La., Pascagoula, Miss. 39567

[21] Appl. No.: 09/066,826

[22] Filed: Apr. 28, 1998

[51] Int. Cl.$^7$ .................................................. A61B 17/04
[52] U.S. Cl. ............................ 606/148; 606/222; 606/139
[58] Field of Search ..................................... 606/222, 228, 606/232, 139–148

[56] References Cited

U.S. PATENT DOCUMENTS

| | | | |
|---|---|---|---|
| 2,108,206 | 2/1938 | Meeker | 128/353 |
| 3,265,069 | 8/1966 | Healey, Jr. et al. | 128/334 |
| 4,553,543 | 11/1985 | Amarasinghe | 128/334 |
| 4,848,367 | 7/1989 | Avant et al. | |
| 4,873,977 | 10/1989 | Avant et al. | |
| 4,911,164 | 3/1990 | Roth | 606/148 |
| 5,047,039 | 9/1991 | Avant et al. | |
| 5,364,408 | 11/1994 | Gordon | 606/144 |
| 5,374,275 | 12/1994 | Bradley et al. | 606/144 |
| 5,403,333 | 4/1995 | Kaster et al. | 606/151 |
| 5,417,699 | 5/1995 | Klein et al. | |
| 5,527,322 | 6/1996 | Klein et al. | |
| 5,613,974 | 3/1997 | Andreas et al. | |
| 5,746,755 | 5/1998 | Wood et al. | |
| 5,779,719 | 7/1998 | Klein et al. | |
| 5,792,152 | 8/1998 | Klein et al. | |
| 5,797,929 | 8/1998 | Andreas et al. | |
| 5,860,991 | 1/1999 | Klein et al. | |

OTHER PUBLICATIONS

Brochure, North American Medical Incorporation, "Urethral Suspension Aiding in Earlier Time to Continence".
Brochure, North American Medical, Incorporation, "Deep Dorsal Venous Ligation—A Unique New Technique".
Greenwald Surgical Company, Inc, entitled "Grip Tip" Suture Guide, Oct. 1998—Greenwald Ad.
Urology 2000 L.L.C., entitled Urology 2000 "DDV Ligator", product data sheet (2 pages).

*Primary Examiner*—Michael Buiz
*Assistant Examiner*—Wen Ngo
*Attorney, Agent, or Firm*—Wenderoth, Lind & Ponack, L.L.P.

[57] ABSTRACT

An anastomotic instrument is provided for use in the performance of an anastomosis after a prostate has been removed. The instrument has an elongated housing, and an end plate fixed at an end of the housing. Provided in the end plate are a plurality of needle guide holes. A needle driving plunger is provided in the housing to move needles loaded in the instrument through the needle guide holes. The plunger is advanced by a plunger rod connected to an actuator mechanism upon depression thereof by a surgeon. An end cap is detachably connected to the housing for the purpose of covering exposed tips of the needles loaded in the housing.

15 Claims, 6 Drawing Sheets

NEEDLE EYE

ANASTOMOTIC INSTRUMENT

BACKGROUND OF THE INVENTION

The present invention relates to an instrument used in a surgical procedure requiring suturing, and more particularly, to an instrument used during the performance of a vesico-urethral anastomosis after a patient's prostate has been removed during a Radical Retropubic Prostatectomy.

Following removal of the prostate, with the instrument of the present invention, a plurality of sutures are placed through the stump of the urethra. The stump of the urethra is then sutured to the bladder. The connection between the urethra and the bladder allows urine to flow from the bladder and out of the urethra after surgery.

Providing this connection is particularly difficult due to the limited working space and the small size of the urethra. The size of the urethra makes it difficult to accurately place the suture thread through the wall of the urethra. The anastomotic instrument of my invention greatly simplifies this procedure for the surgeon.

SUMMARY OF THE INVENTION

According to the present invention, an anastomotic instrument is provided for the purpose of facilitating the anastomosis (connection) between the stump of the urethra and the bladder following removal of the prostate.

The preferred embodiment of my instrument includes an elongated curved housing which is adapted to be inserted in the urethra. A plunger rod extends through the interior of the housing into engagement with a needle driving plunger or piston which is inserted in the housing so as to be slidable therein. The needle driving plunger engages the butt end of a plurality of surgical needles and drives the needles outwardly of the housing.

The housing has a first end which is closed by a perforated closure member, such as an end plate, whose apertures align and guide the needles out of the housing when ejected from the instrument. Typically, four apertures or needle guide holes are provided in the closure member, but other embodiments are contemplated having more or less needle guide holes. The first end of the housing may also include a fastening mechanism for securing an end cap on the housing.

The second end of the housing is that end of the housing which is gripped by the surgeon. The plunger rod is connected to an actuating member, such as an actuating handle, at the second end of the housing. The actuating member is constructed to allow the surgeon to fire or eject the needles from the housing.

In order to fire the needles outwardly of the housing, the actuating member is depressed which moves the needle driving plunger forward in the housing and ejects the needles through the guide holes formed in the closure member.

BRIEF DESCRIPTION OF THE DRAWINGS

These and other features of the present invention will be described with reference to the following detailed description of the invention and the accompanying drawings in which:

FIGS. 3A, 3B and 3C are end views of the instrument shown in FIG. 2. In particular, FIG. 3A shows an end plate prior to loading the instrument with needles. FIG. 3B shows the end plate with needles loaded for an initial deployment of needles. FIG. 3C shows the end plate loaded with needles for the second deployment;

DETAILED DESCRIPTION OF THE INVENTION

Figure 1:
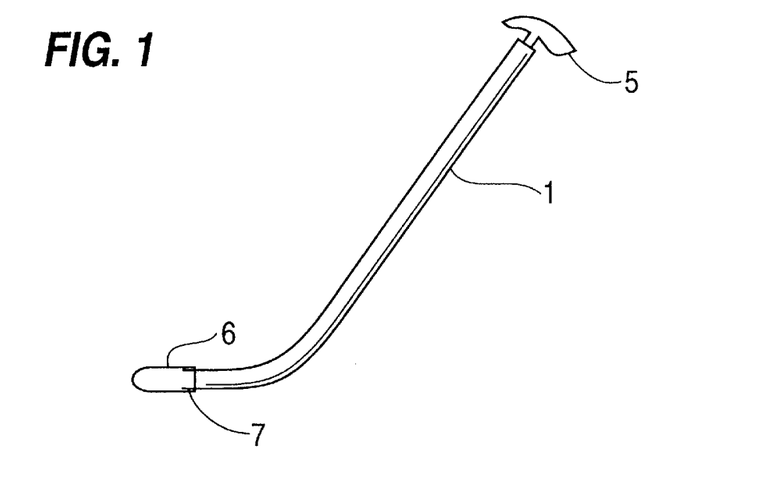
FIG. 1 is a perspective view of an anastomotic instrument having an end cap and constructed in accordance with the preferred embodiment of the present invention.
Figure 5:
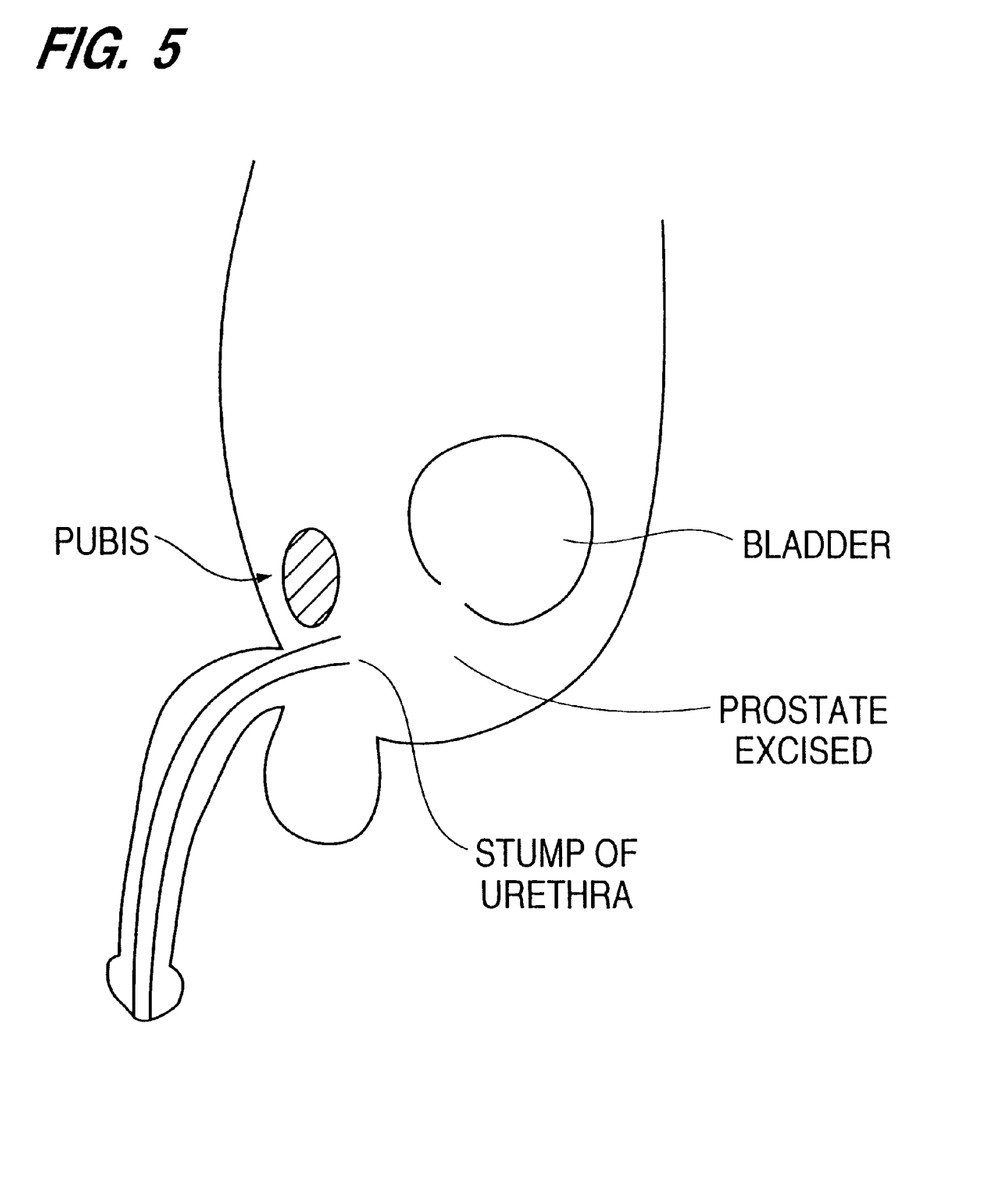
FIG. 5 is a schematic illustration of a relationship of a urethra and a bladder following excision of a prostate.

As shown in FIG. 1, the surgical anastomotic instrument of my preferred invention comprises an elongated curved housing 1, an end cap 6 detachably secured on to the first end of the housing 1 with a fastening means 7, and an actuator handle 5. The instrument is employed for performing a vesico-urethral anastomosis after the prostate has been removed during a Radical Retropubic Prostatectomy (FIG. 5). This connection is necessary to allow the urine to flow out of the urethra after surgery.

Figure 2:
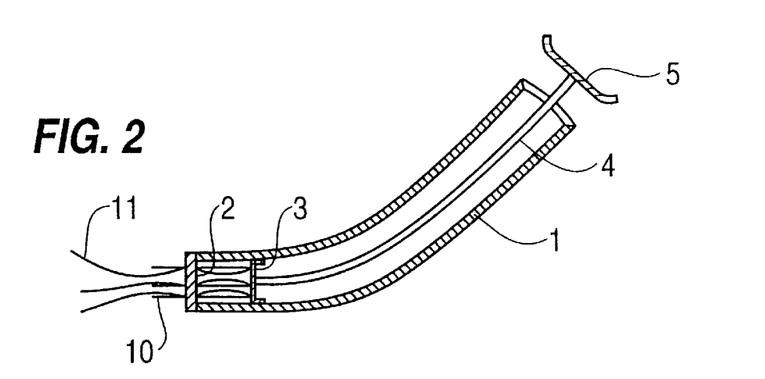
FIG. 2 is a longitudinal cross-sectional view of the anastomotic instrument shown in FIG. 1 with the end cap removed.

As shown in FIG. 2, a plunger rod 4 is disposed within the interior of the housing 1. The first end of the plunger rod 4, which is located proximate to the first end of the housing 1, is connected to a needle driving plunger 3. The second end of the plunger rod 4 located proximate to the second end of the housing 1 is connected to an actuator handle 5. The plunger rod 4 is, in this case, formed of a heavy gauge wire such as stainless steel or other suitable material. Note that the element 4 need not be formed in the shape of a rod but may also take the form of other known mechanisms which are suitable for moving the plunger 3 with respect to the housing. For example, in the event that extreme precision is required with respect to the distance that the needles are advanced, the element 4 may be threadedly engaged with the housing such that movement of the needle driving plunger 3 is effected by rotating the element 4. The plunger 3 could be threadedly engaged with the interior peripheral wall of the housing 1 such that rotation of the actuator 5 would advance or retract the plunger 3. Alternatively, a ratchet and pawl mechanism could be employed to effect advancement of the plunger 3 in the housing 1. It would be apparent to any person having skill in this art field that there are various designs would be effective for a plunger advancement device.

The plunger 3 is inserted in the first end of the housing 1 so as to be in slidable engagement with an interior peripheral surface of the housing 1. The plunger 3 is generally a solid plate-like member which may include an outer annular projecting wall or skirt. The annular projecting wall may project rearwardly of the plate-like member to maintain the plunger 3 in a substantially perpendicular orientation relative to the longitudinal central axis of the housing 1. The front surface of the plunger 3 facing the trailing ends of the needles may be flat or have recesses or concavities for stabilizing or holding the trailing ends of the needles therein.

The actuator 5 may be any conventional mechanism so long as its construction allows the surgeon to move the plunger rod 4 and needle driving plunger 3 back and forth within the housing 1, thereby permitting the needles 10 to be ejected from the housing 1 or drawn inside of the housing 1. A simple construction for an actuator 5 which is in the form of a handle for the surgeon to grip is shown in FIG. 2. Alternatively, the handle may be formed as part of the housing, and the actuator 5 may be a button, lever or other device which is slidably engaged within the handle.

It is also contemplated that the plunger 3, plunger rod 4 and actuator 5 may be an integral structure formed from several components, or these features may be a integrally molded from a material such as plastic so as to form a single unitary structure.

Figure 3A:
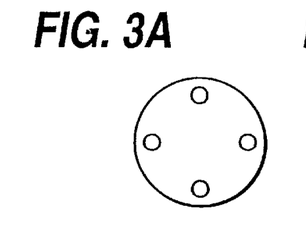

A closure member, in this case an end plate 2, is fixed in the first end of the housing 1. The end plate 2 includes a plurality of apertures or guide holes 9, as shown in FIG. 3A. Each of the guide holes 9 extend completely through the end plate 2. The number and position of the guide holes 9 provided in the end plate 2 is not critical. Typically, four to six guide holes 9, spaced equally around the outer edge of the end plate 2, is preferable. More preferably, four guide holes 9 are formed in the end plate 2 and located at the 12 o'clock, 3 o'clock, 6 o'clock and 9 o'clock positions, i.e. at 90 degree intervals. See FIG. 3A. However it is envisioned that the end plate 2 may be provided instead with only one, two or three guide holes 9. The guide holes 9 are sized and positioned so as to accurately locate and guide movement of surgical needles 10 inserted in the apertures 9. Preferably, the side walls of the guide holes 9 are angled outwardly to allow the needles 10, when ejected from the housing 1, to pierce through the urethral wall.

The end cap 6 is secured to the first end of the housing 1 so as to cover the projecting ends of the loaded needles 10. Suture thread 11, which is attached to each of the needles, may be contained within the interior of the end cap 6 prior to insertion of the instrument into the urethra. The end cap 6 may be provided with an inner structure about which the suture thread 11 can be wound. Alternatively, the suture thread 11 can extend through an opening in the end cap 6 and lie along the length of the housing 1 upon insertion of the housing 1 in a urethra.

The end cap 6 may be fastened on the housing by any suitable fastening means 7, such as a threaded connection, or a quick-release coupling. The particular fastening means 7 employed should permit the cap to be easily removed. If a threaded connection is employed, the fastening means 7 is preferably designed to release the end cap by rotating the cap only through 90 degrees, i.e. a quarter turn.

The surgical anastomotic instrument of the present invention may be constructed from conventional materials for surgical instruments, for example a metal such as stainless steel or plastic. Preferably, the instrument is constructed primarily from plastic materials so that it is inexpensive to manufacture and can be disposal. The instrument may also be sold in a package which is presterilized for surgical use.

Figure 3B:
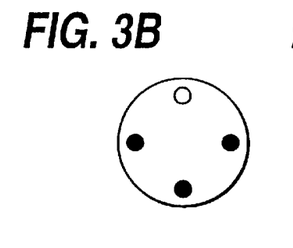

The preferred instrument of the present invention is used by a surgeon in the following manner. Three needles, connected with suture thread, are loaded by the surgeon in the instrument at the 3 o'clock, 6 o'clock and 9 o'clock positions. See FIG. 3B. Then the end cap is secured on the end of the housing so as to cover the leading ends of the loaded needles.

Figure 6:
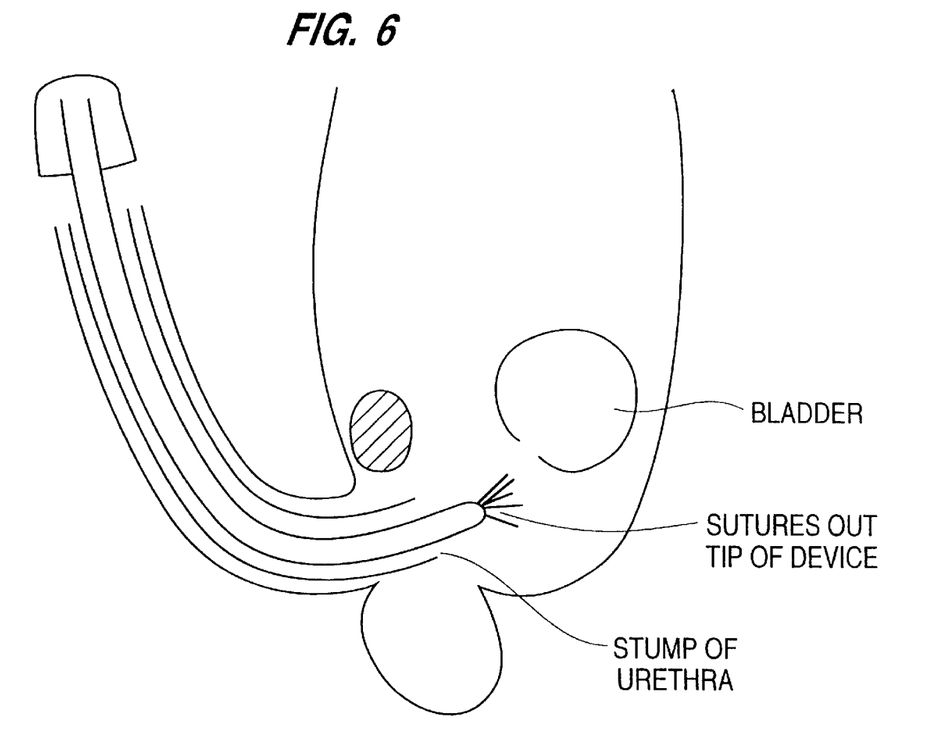
FIG. 6 is a schematic illustration of an anastomotic instrument fully inserted in the urethra.

The loaded instrument is then inserted in the urethra and advanced until the tip of the first end of the housing is pushed through the stump of the urethra (FIG. 6), which stump remains following removal of the prostate. The needles initially loaded in the instrument are intended for placement of a posterior set of sutures. The tip of the first end of the instrument housing, which has been pushed through the stump of the urethra, can be easily visually located by the surgeon. The end cap is then removed so as to expose the needles and suture material.

Figure 7:
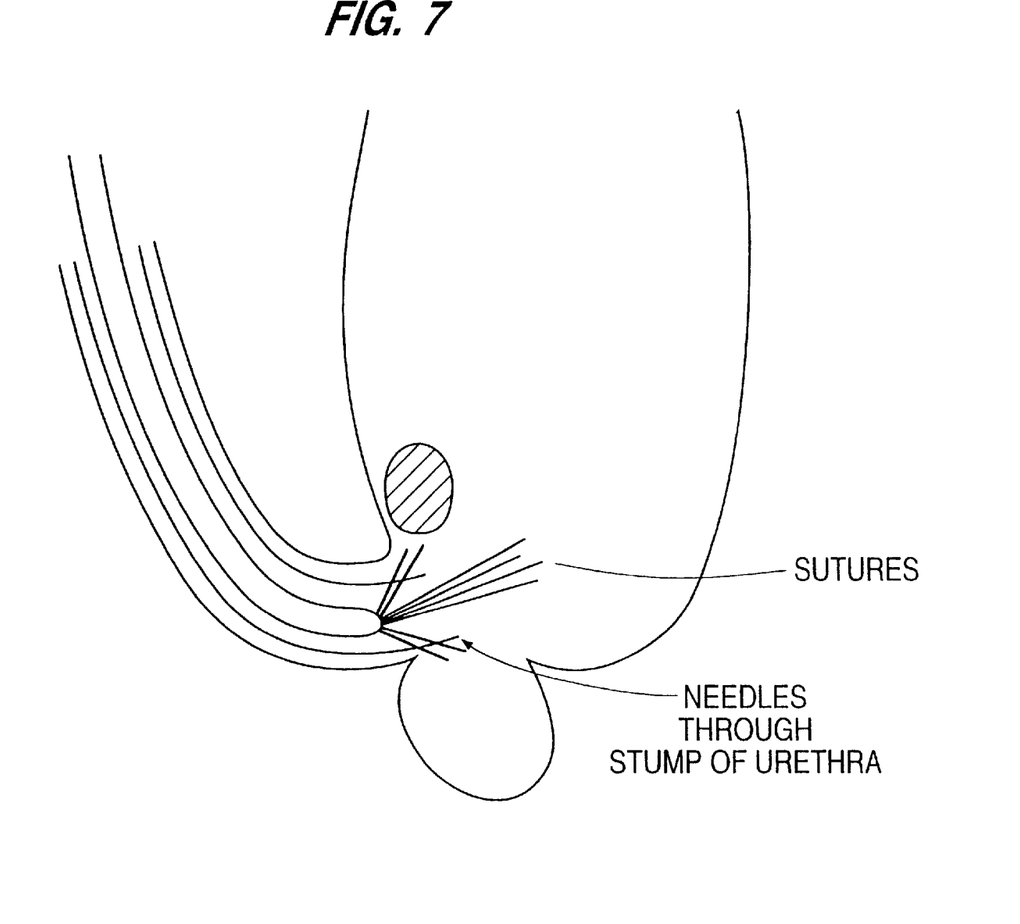
FIG. 7 is a schematic illustration showing the instrument inserted in the urethra and with the needles fired in the initial deployment.

Then the actuator handle is depressed so as to partially deploy the needles a distance of approximately 2–3 mm out of the end of the housing. The instrument is then retracted from the urethra, thus retracting the tips of the needles within the interior of the urethra stump. At this point, the needle tips are located about 1–1.5 cm from the proximal end of the urethra. At this retracted position, the instrument is angled posteriorly, i.e. toward the rectum, and then the actuator handle is fully depressed so as to fire the needles through the stump of the urethra. See FIG. 7. The surgeon then pulls the needles and suture material through the wall of the urethra, and the instrument is removed.

Figure 3C:
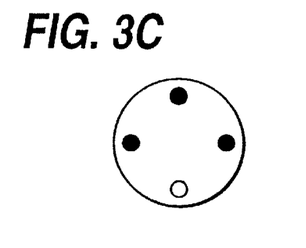
Figure 4:
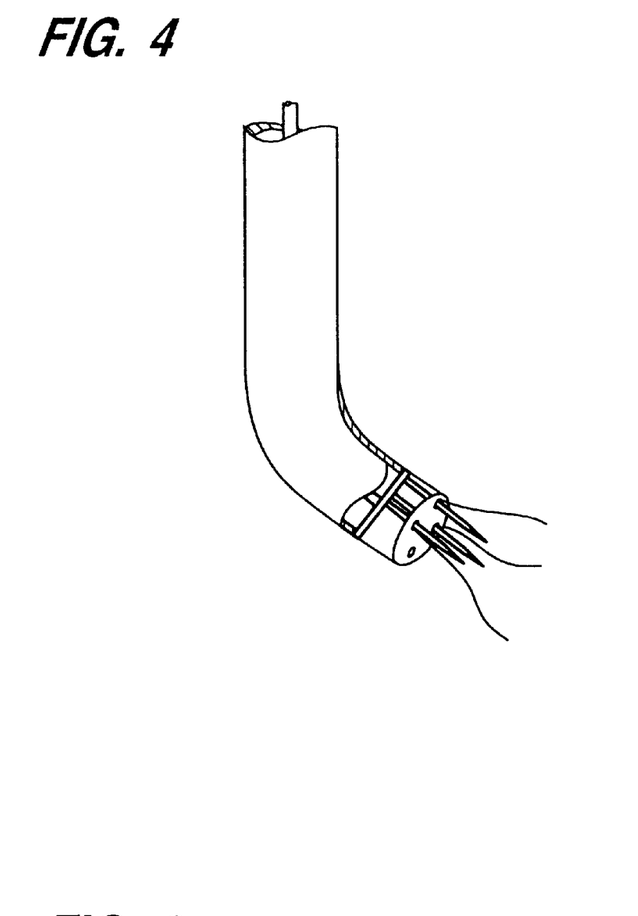
FIG. 4 is a partial cross-sectional perspective view showing the instrument loaded with needles for the second deployment.

After removal of the instrument from the urethra, the instrument is loaded a second time with three more needles and suture thread for placement of an anterior set of sutures. As shown in FIG. 3C and FIG. 4, this second deployment of needles are located in the end plate at the 12 o'clock, 3 o'clock, and 9 o'clock positions. Then the end cap is installed on the housing and the above procedure is repeated, except that the retracted instrument is angled anteriorly, i.e. toward the front of the patient, and then the needles are fully deployed through the stump of the urethra.

Following the above-described first and second needle deployments, a curved needle is attached to the loose end of the suture thread of each needle and that end of the suture thread is sutured to the bladder. The sutures are tied individually in a conventional manner, drawing the stump of the urethra and the bladder tightly together, and a catheter is placed.

While the foregoing description explains the preferred embodiment of my instrument, several alternative embodiments of my anastomotic instrument are also contemplated and their descriptions follow.

The first alternative embodiment of the instrument is different from my preferred embodiment in that it enables the surgeon to perform the anastomosis procedure with a single deployment of needles. More specifically, the instrument is provided with a sufficient number of guide holes and needles, for example four to six, to suture the stump of the urethra to the bladder with a single deployment of needles. The side walls of the guide holes are angled outwardly at a suitable angle to eliminate the need for angling the instrument anteriorly or posteriorly as described above in the two step deployment method. The instrument is loaded with the needles and suture threads, and the procedure is performed as described above, except that the needles are ejected through the urethral wall in a single deployment.

A second alternative embodiment of my anastomotic instrument is different from my preferred embodiment in that it enables the surgeon to perform the anastomotic procedure in a two step deployment method as described above without reloading the instrument. More specifically, the instrument is constructed with two independent plunger, plunger rod and actuator handle mechanisms which allow for separate firings of two groups of needles. The surgeon depresses a first actuator mechanism in the actuator handle to fire a first set of needles, preferably two or three in number, in the first deployment. The surgeon then depresses a second actuator mechanism in the actuator handle to separately fire a second set of needles, again preferably two or three in number, in the second deployment.

Figure 8:
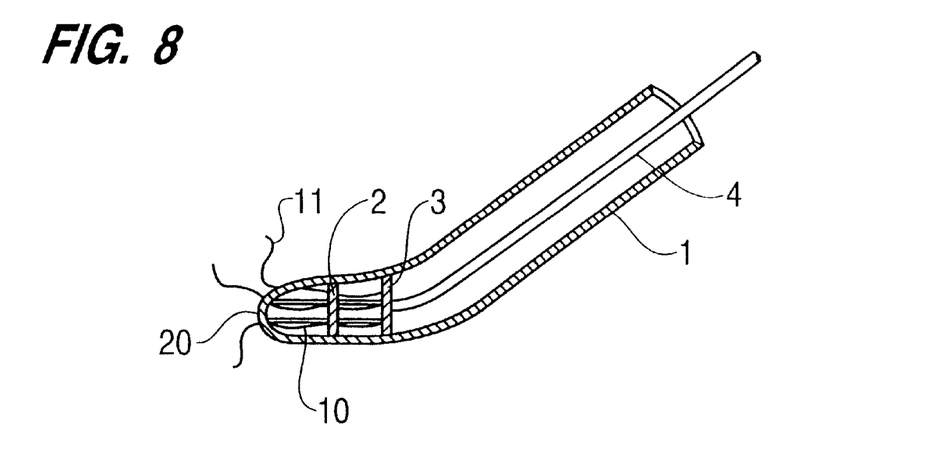
FIG. 8 is a longitudinal cross-sectional view of an alternate embodiment of an anastomotic instrument of the present invention.

A third alternative embodiment, shown in FIG. 8, of the anastomotic instrument is primarily composed of inexpensive materials such as plastic so that it is disposable. The instrument is sold in a sterilized package and is preloaded with a plurality of needles and suture threads. The instrument possesses an integral rounded tip 20 which is provided with a plurality of needle guide holes through which the needles and suture are ejected. The integral rounded tip 20 is not removable from the housing, that is, this embodiment of my instrument does not contain a removable end cap or end plate. The integral rounded tip essentially combines the functions of the closure member and end cap of the preferred embodiment described above. More specifically, the rounded tip serves the function of the end cap in easing insertion of the instrument into the urethra and in shielding the leading ends of the needles from the urethra lumen. The tip also serves the function of the end plate in guiding the needles in proper alignment through the urethra wall upon deployment. Hence, although the instrument shown in FIG. 8 employs an end plate 2, it can be constructed without the end plate because the integral rounded tip 20 can perform the guiding function.

In the instrument shown in FIG. 8, the needles and suture thread may be pre-loaded in the housing. The rounded tip is integrally attached to the housing to enclose the needles and suture thread. As noted above, the rounded tip, which contains a plurality of guide holes, serves to guide the needles outwardly through the urethra stump during firing. Upon deployment of the needles, the instrument is disposed of. The instrument may be designed for performing the anastomosis procedure in a single deployment or in two deployments. If in two deployments, the surgeon will use a first preloaded disposable instrument for the first deployment, and the surgeon will use a second preloaded disposable instrument for the second deployment.

Figure 9:
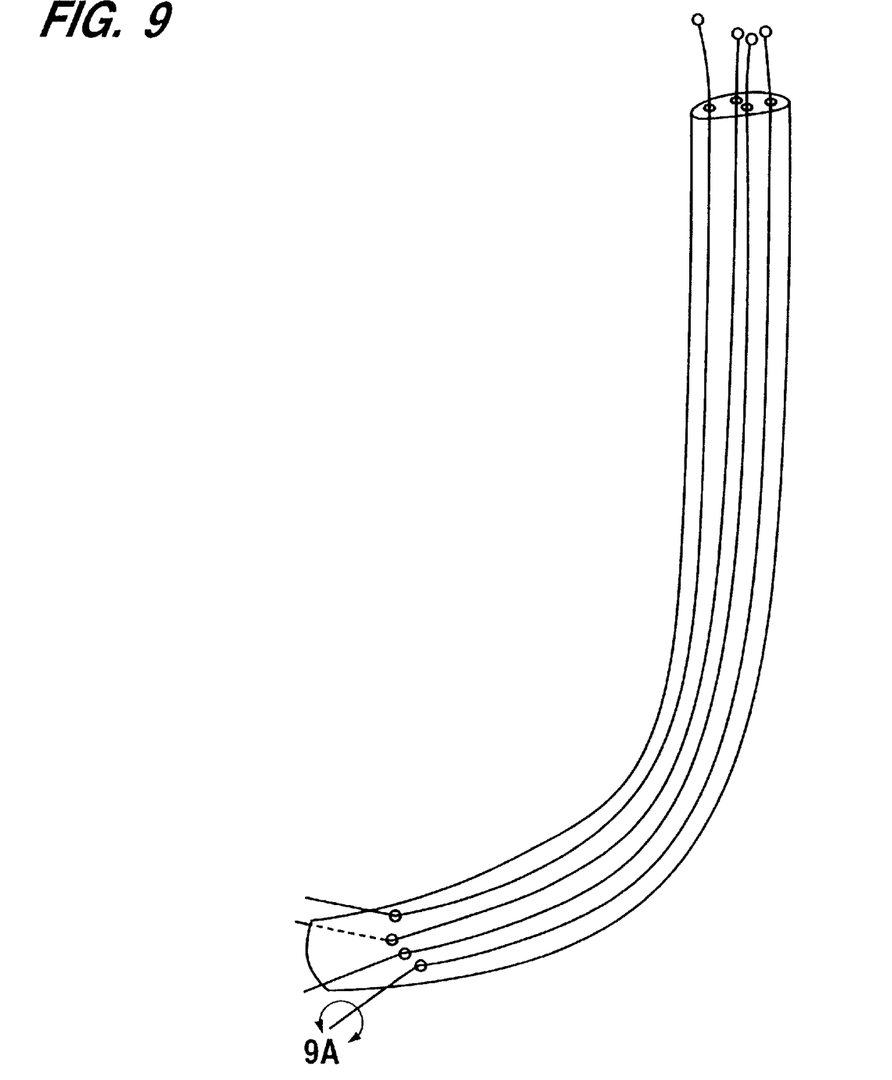
FIG. 9 shows a further embodiment of an anastomotic instrument of the present invention.
Figure 9A:
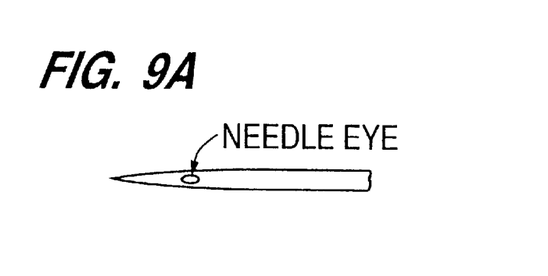

A fourth alternative embodiment of the anastomotic instrument is shown in FIG. 9 and is different from the preferred embodiment in that it does not require an end cap, end plate or plunger. This instrument is comprised of a housing and a plurality of plunger rods. The second ends of the plunger rods are proximate to the second end of the housing and each have an actuator mechanism. For example, the plunger rods may have a simple ball shaped attachment which can be gripped by the surgeon as shown in FIG. 9. Alternatively, the actuator mechanisms may be button- or lever-type devices which are slidably engaged with a handle. The first ends of the plunger rods each have permanently attached thereto a needle having a needle eye. The first end of the housing has a rounded tip which is provided with a plurality of apertures through which the needles are guided when ejected therefrom. In use, the surgeon inserts the instrument through the urethra in the conventional manner so that the tip of the housing is visible. Then the surgeon depresses the actuator mechanisms independently to partially deploy the needles from the housing to the extent necessary for the eye of the needle to be visible to the surgeon. The sutures are then inserted through the eyes of the needles, and the needles with suture threads are withdrawn back inside of the housing. The instrument is then retracted within the lumen of the urethra until the tip is properly positioned for firing the needles through the proximate end of the urethra stump. The needles are then fired separately through the stump by independently depressing the actuators of each plunger rod until the needle eyes and sutures are passed through the urethra wall. The sutures are then removed from the needles. The needles are retracted back into the instrument. A curved needle is then attached to the sutures, and the urethra stump is tied to the bladder in the conventional manner.

Although the instrument has been described with respect to a specific embodiment, it will be appreciated that various modifications and changes to the instrument are possible with out departing from the invention, the scope of which is defined and set forth in the following claims.

I claim:

1. An anastomotic instrument comprising:
   an elongated housing having a first end and a second end;
   a closure member fixed at said first end of said housing, said closure member having a plurality of needle guide holes extending therethrough;
   a needle driving plunger, slidably disposed in said housing, for moving needles through said needle guide holes;
   a plunger rod having a first end connected to a rear side of said plunger, and a second end extending through said second end of said housing;
   an actuator member connected to said second end of said plunger rod; and
   an end cap detachably connected to said first end of said housing for covering leading ends of needles loaded in said housing and extending through said closure member.

2. The anastomotic instrument as claimed in claim 1, wherein said needle guide holes are located in said closure member at 90 degree intervals.

3. The anastomotic instrument as claimed in claim 1, wherein said end cap is detachably connected to said housing by means of a threaded connection.

4. The anastomotic instrument as claimed in claim 1, wherein said end cap is detachably connected to said housing by means of a quick-release coupling.

5. The anastomotic instrument as claimed in claim 1, wherein said housing is formed so as to have a straight section and a curved section, and is sized so as to be insertable into a urethra.

6. An anastomotic instrument comprising:
   a housing having a hollow elongated body, a front end and a rear end, wherein said front end includes a plurality of guide holes;
   a plurality of needles positioned in said hollow elongated body and extending into said guide holes, respectively;
   a needle driving plunger movable disposed in said housing and contacting a trailing end of each of said needles in order to drive said needles through said guide holes formed in said front end; and
   a plunger advancement device for effecting movement of said needle driving plunger, said plunger advancement device having a first end connected to a rear side of said plunger, and a second end extending through said second end of said housing.

7. The anastomotic instrument as claimed in claim 6, wherein said needle guide holes are located in said front end at 90 degree intervals.

8. The anastomotic instrument as claimed in claim 6, further comprising a plurality of needles engaging said plunger and extending partially into said guide holes, wherein said front end is fixedly attached to said elongated housing body.

9. The anastomotic instrument as claimed in claim 6, wherein said rounded tip end is formed integrally with elongated housing body.

10. The anastomotic instrument as claimed in claim 6, wherein said housing body is formed so as to have a straight section and a curved section, and said housing is sized so as to be insertable into a urethra.

11. The anastomotic instrument as claimed in claim 6, wherein said front end comprises a rounded tip end.

12. The anastomotic instrument as claimed in claim 1, further comprising a plurality of needles engaging said plunger and extending through said needle guide holes, respectively.

13. The anastomotic instrument as claimed in claim 1, further comprising a plurality of suturing devices disposed in said housing and extending through said needle guide holes, respectively, wherein each of said suturing devices has a leading end and a trailing end, which is in engagement with said plunger, and wherein said leading ends of said suturing devices are completely enclosed by said end cap when it is installed on said housing.

14. The anastomotic instrument as claimed in claim 1, wherein said elongated housing comprises a hollow tubular member, and said closure member comprises a circular plate extending across the first end of said hollow tubular member.

15. The anastomotic instrument as claimed in claim 14, wherein a peripheral edge portion of said circular plate is connected to the front end of said hollow tubular member.

* * * * *